United States Patent [19]

Umezawa et al.

[11] 4,332,794

[45] Jun. 1, 1982

[54] 6"-DEOXYDIBEKACIN, 4",6"-DIDEOXYDIBEKACIN AND 1-N-AMINOACYL DERIVATIVES THEREOF, AND THE PRODUCTION OF THESE NEW COMPOUNDS

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 174,630

[22] Filed: Aug. 1, 1980

[30] Foreign Application Priority Data

Sep. 19, 1979 [JP] Japan ................. 54/119323

[51] Int. Cl.$^3$ ............... A61K 31/71; C07H 15/22
[52] U.S. Cl. .................... 424/180; 424/181; 536/13.7; 536/13.8
[58] Field of Search ................. 536/10; 424/180

[56] References Cited

U.S. PATENT DOCUMENTS

| | | | |
|---|---|---|---|
| 3,929,762 | 12/1975 | Umezawa et al. | 536/10 |
| 4,020,269 | 4/1977 | Hiraga et al. | 536/10 |
| 4,029,883 | 6/1977 | Hiraga et al. | 536/10 |
| 4,051,315 | 9/1977 | Godfrey et al. | 536/10 |
| 4,156,078 | 5/1979 | Umezawa et al. | 536/10 |

*Primary Examiner*—Johnnie R. Brown
*Attorney, Agent, or Firm*—Larson and Taylor

[57] ABSTRACT

New compounds, 6"-deoxydibekacin, 4", 6"-dideoxydibekacin, 1-N-(L-4-amino-2-hydroxybutyryl)-6"-deoxydibekacin and 1-N-(L-4-amino-2-hydroxybutyryl)-4",6"-dideoxydibekacin are now produced semi-synthetically from dibekacin, i.e. 3',4'-dideoxykanamycin B. These four new compounds are each useful as an antibacterial agent. Production of 6"-deoxydibekacin or 4",6"-dideoxydibekacin is made by removal of the 6"-hydroxyl group or by removal of the 4"- and 6"-hydroxyl groups from an amino-protected and hydroxyl-protected derivative of dibekacin. Production of 1-N-(L-4-amino-2-hydroxybutyryl)-6"-deoxydibekacin or -4",6"-dideoxydibekacin is made by acylating the 1-amino group of 6"-deoxydibekacin or 4",6"-dideoxydibekacin with the L-4-amino-2-hydroxybutyryl group, or alternatively by removal of the 6"-hydroxyl group or the 4"- and 6"-hydroxyl groups from a known compound, 1-N-(L-4-amino-2-hydroxybutyryl)-dibekacin.

9 Claims, No Drawings

6''-DEOXYDIBEKACIN, 4'',6''-DIDEOXYDIBEKACIN AND 1-N-AMINOACYL DERIVATIVES THEREOF, AND THE PRODUCTION OF THESE NEW COMPOUNDS

BACKGROUND OF THE INVENTION

1. Field of the Invention

This invention relates to new semi-synthetic aminoglycosidic antibiotics, particularly 6''-deoxydibekacin, 4'',6''-dideoxydibekacin, 1-N-(L-4-amino-2-hydroxybutyryl)-6''-deoxydibekacin and 1-N-(L-4-amino-2-hydroxybutyryl)-4'',6''-dideoxydibekacin which are each the new compound useful as antibacterial agents. This invention also relates to processes for the production of these new compounds. This invention further relates to an antibacterial composition comprising one of these new compounds as the active ingredient.

2. Description of the Prior Art

Dibekacin, namely 3',4'-dideoxykanamycin B was semi-synthetically produced from kanamycin B by the present inventors (see Japanese patent publication No. 7595/75; Japanese Pat. No. 794,612; U.S. Pat. No. 3,753,973). Dibekacin has been used extensively in therapeutic treatment of various bacterial infections as a chemotherapeutic agent which is active against the kanamycin-sensitive bacteria and also against various kanamycin-resistant bacteria. We, the present inventors, produced semi-synthetically 1-N-(L-4-amino-2-hydroxybutyryl)-dibekacin which is a chemotherapeutic agent effective against dibekacin-resistant bacteria (see Japanese patent publication No. 33,629/77; U.S. Pat. No. 4,107,424). Recently, we also produced semi-synthetically 6''-deoxyamikacin (i.e. 1-N-(L-4-amino-2-hydroxybutyryl)-6''-deoxykanamycin A) and 4'',6''-dideoxyamikacin (i.e. 1-N-(L-4-amino-2-hydroxybutyryl)-4'',6''-dideoxykanamycin A) (Japanese patent application No. 54733/79) which each have a low oto-toxicity and are confirmed to show an antibacterial activity as high as that of amikacin, namely 1-N-(L-4-amino-2-hydroxybutyryl)-kanamycin A.

SUMMARY OF THE INVENTION

In our further researches, we have now succeeded at first time in synthetically producing the new 6''-deoxy or 4'',6''-dideoxy derivatives of dibekacin and 1-N-(L-4-amino-2-hydroxybutyryl)-dibekacin, respectively. Furthermore, we have found that these new 6''-deoxy derivatives and 4'',6''-dideoxy derivatives now synthetized exhibit not only a low oto-toxicity but also show an antibacterial activity as high as that of dibekacin or 1-N-(L-4-amino-2-hydroxybutyryl)-dibekacin.

DETAILED DESCRIPTION OF THE INVENTION

According to a first aspect of this invention, therefore, there is provided as a new compound a deoxy derivative of dibekacin represented by the general formula (I)

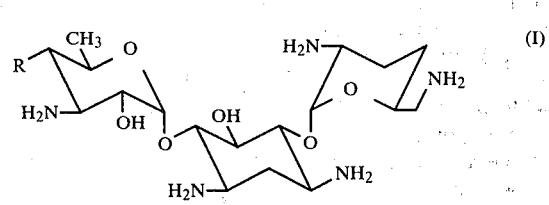

wherein R is a hydroxyl group or a hydrogen atom, and an acid addition salt thereof. The new compound of the above formula (I) where R is a hydroxyl group is 6''-deoxydibekacin, and the new compound of the formula (I) where R is a hydrogen atom is 4'',6''-dideoxydibekacin.

According to a second aspect of this invention, there is provided as a new compound a deoxy derivative of 1-N-(L-4-amino-2-hydroxybutyryl)-dibekacin represented by the general formula (II)

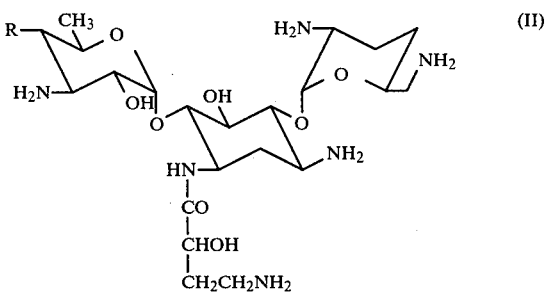

wherein R is a hydroxyl group or a hydrogen atom, and an acid addition salt thereof. The new compound of the above formula (II) where R is a hydroxyl group is 1-N-(L-4-amino-2-hydroxybutyryl)-6''-deoxydibekacin, and the new compound of the formula (II) where R is a hydrogen atom is 1-N-(L-4-amino-2-hydroxybutyryl)-4'',6''-dideoxydibekacin.

The physico-chemical and biological properties of the above-mentioned four new compounds according to the first and second aspects of this invention are as follows:

(1) 6''-Deoxydibekacin sesqui-carbonate is a substance in the form of a colorless powder decomposing gradually near 131° C. and showing a specific optical rotation $[\alpha]_D^{26} = +101°$ (c 0.44, water). Its elemental analysis is coincident with the theoretical values of $C_{18}H_{37}N_5O_7 \cdot 3/2H_2CO_3$ (C 44.31%, H 7.63%, N 13.25%). In mass spectrometry, it gave a value of m/e 435 (M+). This substance gives a single spot (positive to ninhydrin) at Rf 0.38 in a thin layer chromatography on silica gel developed with a mixture of butanol-ethanol-chloroform-water (4:5:2:5 by volume) as the development solvent.

(2) 4'',6''-Dideoxydibekacin sesqui-carbonate is a substance in the form of a colorless powder decomposing gradually near 129° C. and showing a specific optical rotation $[\alpha]_D^{23} = +126°$ (c 0.5, water). Its elemental analysis is coincident with the theoretical values of $C_{18}H_{37}N_5O_6 \cdot 3/2 \, H_2CO_3$ (C 45.69%, H 7.87%, N 13.66%). In mass spectrometery, it gave a value of m/e 420 (M+1)+. This substance gives a single spot (positive to ninhydrin) at Rf 0.45 in the above-mentioned silica gel thin layer chromatography.

(3) 1-N-(L-4-amino-2-hydroxybutyryl)-6''-deoxydibekacin sesqui-carbonate is a substance in the form of a colorless powder decomposing at 132°–139° C. and showing a specific optical rotation $[\alpha]_D^{23} = +73°$ (c 0.3, water). Its elemental analysis is coincident with the theoretical values of $C_{22}H_{42}N_6O_9.3/2H_2CO_3$ (C 44.97%, H 7.23%, N 13.39%). This substance gives a single spot (positive to ninhydrin) at Rf 0.10 in the above-mentioned silica gel thin layer chromatography.

(4) 1-N-(L-4-amino-2-hydroxybutyryl)-4″,6″-dideoxydibekacin sesqui-carbonate is a substance in the form of a colorless powder having a decomposition point at 142°~147° C. and showing a specific optical rotation $[\alpha]_D^{24} = +84°$ (c 0.5, water). Its elemental analysis is coincident with the theoretical values of $C_{22}H_{42}N_6O_8.3/2\ H_2CO_3$ (C 46.15%, H 7.42%, N 13.74%). This substance gives a single spot at Rf 0.21 in the above-mentioned silica gel thin layer chromatography.

The minimum inhibitory concentrations (mcg/ml) of 6″-deoxydibekacin (abbreviated as 6″-DDKB), 4″,6″-dideoxydibekacin (abbreviated as 4″,6″-DDKB), 1-N-(L-4-amino-2-hydroxybutyryl)-6″-deoxydibekacin (abbreviated as AHB-6″-DDKB) and 1-N-(L-4-amino-2-hydroxybutyryl)-4″,6″-dideoxydibekacin (abbreviated as AHB-4″,6″-DDKB) of this invention against various microorganisms were determined according to serial dilution method on a nutrient agar medium at 37° C., the estimation being made after 18 hours incubation. For comparison purpose, the minimum inhibitory concentrations of dibekacin (abbreviated as DKB) were also determined in the same manner as stated above.

The antibacterial spectra of these new and known substances are shown in Table 1 below.

TABLE 1

| Test organisms | MIC. (mcg/ml) | | | | |
|---|---|---|---|---|---|
| | DKB | 6″-DDKB | 4″,6″-DDKB | AHB-6″-DDKB | AHB-4″,6″-DDKB |
| *Staphylococcus aureus* 209P | 0.78 | 0.78 | 0.39 | 1.56 | 0.78 |
| *Staphylococcus aureus* Smith | <0.20 | <0.20 | <0.20 | <0.20 | <0.20 |
| *Staphylococcus aureus* APO1 | 1.56 | 3.13 | 3.13 | 1.56 | 1.56 |
| *Staphylococcus epidermidis* 109 | 1.56 | 1.56 | 3.13 | 1.56 | 1.56 |
| *Mycrococcus flavus* FDA 16 | 100 | 25 | 50 | 1.56 | 1.56 |
| *Sarcina lutea* PCI 1001 | 100 | 25 | 50 | 3.13 | 3.13 |
| *Bacillus anthracis* | <0.20 | 0.39 | <0.20 | 0.20 | <0.20 |
| *Bacillus subtilis* PCI 219 | <0.20 | <0.20 | <0.20 | <0.20 | <0.20 |
| *Bacillus subtilis* NRRL B-558 | <0.20 | <0.20 | <0.20 | <0.20 | <0.20 |
| *Bacillus cereus* ATCC 10702 | 3.13 | 6.25 | 6.25 | 3.13 | 1.56 |
| *Corynebacterium bovis* 1810 | 50 | 25 | 50 | 3.13 | 6.25 |
| *Mycobacterium smegmatis* ATCC 607 | 1.56 | 0.78 | 1.56 | 0.39 | 0.39 |
| *Escherichia coli* NIHJ | 1.56 | 1.56 | 1.56 | 1.56 | 1.56 |
| *Escherichia coli* K-12 | 1.56 | 1.56 | 1.56 | 1.56 | 1.56 |
| *Escherichia coli* K-12 R5 | >100 | 100 | >100 | 50 | 100 |
| *Escherichia coli* K-12 R 388 | 1.56 | 1.56 | 1.56 | 0.78 | 0.78 |
| *Escherichia coli* K-12 J5B 11-2 | 3.13 | 1.56 | 3.13 | 1.56 | 1.56 |
| *Escherichia coli* K-12 ML 1629 | 3.13 | 1.56 | 3.13 | 1.56 | 1.56 |
| *Escherichia coli* K-12 ML 1630 | 3.13 | 3.13 | 3.13 | 3.13 | 1.56 |
| *Escherichia coli* K-12 ML 1410 | 1.56 | 3.13 | 1.56 | 3.13 | 1.56 |
| *Escherichia coli* K-12 1410 R81 | 1.56 | 1.56 | 1.56 | 1.56 | 1.56 |
| *Escherichia coli* K-12 LA 290 R55 | 100 | >100 | 100 | 3.13 | 1.56 |
| *Escherichia coli* K-12 LA 290 R56 | 25 | 25 | 50 | 1.56 | 1.56 |
| *Escherichia coli* K-12 LA 290 R64 | 25 | 25 | 25 | 1.56 | 0.78 |
| *Escherichia coli* W677 | 1.56 | 1.56 | 0.78 | 1.56 | 1.56 |
| *Escherichia coli* JR66/W677 | 100 | 100 | 100 | 3.13 | 3.13 |
| *Escherichia coli* K-12 C 600R/35 | 1.56 | 3.13 | 50 | 1.56 | 0.78 |
| *Escherichia coli* JR255 | >100 | >100 | 100 | 1.56 | 1.56 |
| *Klebsiella pneumoniae* PCI 602 | 0.78 | 1.56 | 0.78 | 1.56 | 0.78 |
| *Klebsiella pneumoniae* 22 #3038 | 100 | 100 | 100 | 3.13 | 3.13 |
| *Shigella dysenteriae* JS11910 | 3.13 | 3.13 | 3.13 | 6.25 | 3.13 |
| *Shigella flexneri* 4b JS11811 | 3.13 | 3.13 | 3.13 | 6.25 | 6.25 |
| *Shigella sonnei* JS11746 | 6.25 | 3.13 | 3.13 | 6.25 | 3.13 |
| *Salmonella typhi* F63 | 0.78 | 0.39 | 0.78 | 0.39 | 0.39 |
| *Salmonella enteritidis* 1891 | 3.13 | 3.13 | 6.25 | 3.13 | 6.25 |
| *Proteus vulgaris* OX19 | 0.78 | 0.39 | 0.78 | 0.78 | 0.39 |
| *Proteus rettgeri* GN311 | 6.25 | 6.25 | 3.13 | 50 | 25 |
| *Proteus rettgeri* GN466 | 1.56 | 3.13 | 1.56 | 12.5 | 3.13 |
| *Serratia marcescens* | 100 | 100 | 100 | 50 | 100 |
| Serratia SOU | >100 | >100 | >100 | 100 | >100 |
| Serratia 4 | 100 | 100 | 100 | 6.25 | 6.25 |
| Providencia Pv 16 | >100 | >100 | >100 | 25 | 25 |
| Providencia 2991 | >100 | >100 | >100 | 100 | 100 |
| *Pseudomonas aeruginosa* A3 | 3.13 | 1.56 | 3.13 | 3.13 | 1.56 |
| *Pseudomonas aeruginosa* No. 12 | 6.25 | 6.25 | 12.5 | 25 | 12.5 |
| *Pseudomonas aeruginosa* H9 | 6.25 | 12.5 | 100 | 6.25 | 6.25 |
| *Pseudomonas aeruginosa* H11 | 12.5 | 12.5 | 100 | 50 | 50 |
| *Pseudomonas aeruginosa* TI-13 | 6.25 | 12.5 | 100 | 6.25 | 25 |
| *Pseudomonas aeruginosa* GN315 | >100 | 100 | >100 | 50 | 100 |
| *Pseudomonas aeruginosa* 99 | 50 | 12.5 | >100 | 12.5 | 12.5 |
| *Pseudomonas aeruginosa* B-13 | 6.25 | 50 | >100 | 25 | 12.5 |
| *Pseudomonas aeruginosa* 21-75 | >100 | >100 | >100 | 100 | >100 |
| *Pseudomonas aeruginosa* PST1 | >100 | >100 | >100 | 50 | 25 |
| *Pseudomonas aeruginosa* ROS134/PU21 | >100 | >100 | >100 | >100 | >100 |
| *Pseudomonas aeruginosa* K-Ps102 | 6.25 | 6.25 | 25 | 12.5 | 12.5 |
| *Pseudomonas maltophilia* GN907 | >100 | >100 | >100 | >100 | >100 |

From the above table, it is seen that the new compounds of the general formulae (I) and (II) according to this invention inhibit the growth of many kinds of bacterial strains. The new compounds of this invention exhibit a low acute toxicity to animals and men. It has been estimated that the intravenous LD$_{50}$ of 6″-deoxydibekacin and 4″,6″-dideoxydibekacin in mice were more than 60 mg/kg, and also that the intravenous LD$_{50}$ of 1-N-(L-4-amino-2-hydroxybutyryl)-6″-deoxydibekacin and 1-N-(L-4-amino-2-hydroxybutyryl)-4″,6″-dideoxydibekacin in mice were more than 80 mg/kg.

As compared to dibekacin (DKB), 6″-deoxydibekacin and 4″,6″-dideoxydibekacin of this invention are same or more active against kanamycin-sensitive and resistant bacteria. 1-N-(L-4-Amino-2-hydroxybutyryl)-6″-deoxydibekacin and 1-N-(L-4-amino-2-hydroxybutyryl)-4″,6″-dideoxydibekacin of this invention show a similar activity to that of 1-N-(L-4-amino-2-hydroxybutyryl)-dibekacin. Bisides, 6″-deoxydibekacin, 4″,6″-dideoxydibekacin, 1-N-(L-4-amino-2-hydroxybutyryl)-6″-deoxydibekacin and 1-N-(L-4-amino-2-hydroxybutyryl)-4″,6″-dideoxydibekacin of this invention have a low oto-toxicity.

The new compounds of this invention, that is, 6″-deoxydibekacin, 4″,6″-dideoxydibekacin, 1-N-(L-4-amino-2-hydroxybutyryl)-6″-deoxydibekacin and 1-N-(L-4-amino-2-hydroxybutyryl)-4″,6″-dideoxydibekacin are usually obtained in the form of its free base or a hydrate or a carbonate thereof. The new compounds of this invention each may readily be converted into a form of a pharmaceutically acceptable acid addition salt thereof, such as the hydrochloride, hydrobromide, sulfate, phosphate, nitrate, acetate, maleate, citrate, ascorbate, methanesulfonate and the like by reacting with the appropriate, pharmaceutically acceptable inorganic or organic acid in an aqueous medium.

The new compounds of the formula (I) or (II) according to this invention and its pharmaceutically acceptable acid addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.1 to 1 g. per person a day when it is given orally. It is preferred that said dose should be orally administered in three to four aliquots per day. The new compounds of this invention may also be administered by intramuscular injection at a dosage of 50 to 500 mg per person two to four times per day. Moreover, the new compounds of this invention may be formulated into an ointment for external application which contains the active compound at a concentration of 0.5~5% by weight in mixture with a known ointment base such as polyethylene glycol. Furthermore, the new compounds of this invention are each useful for sterilization of surgical instruments and sanitary materials.

According to a third aspect of this invention, therefore, there is provided an antibacterial composition comprising as the active ingredient 6″-deoxydibekacin, 4″,6″-dideoxydibekacin, 1-N-(L-4-amino-2-hydroxybutyryl)-6″-deoxydibekacin or 1-N-(L-4-amino-2-hydroxybutyryl)-4″,6″-dideoxydibekacin or a pharmaceutically acceptable acid addition salt thereof, in an antibacterially effective amount to inhibit the growth of bacteria, in combination with a carrier for the active ingredient compound.

Next, the production of the new compounds of the formula (I) or (II) according to this invention is described.

6″-Deoxydibekacin and 4″,6″-dideoxydibekacin may be produced semi-synthetically starting from dibekacin. 1-N-(L-4-Amino-2-hydroxybutyryl)-6″-deoxydibekacin and 1-N-(L-4-amino-2-hydroxybutyryl)-4″,6″-dideoxydibekacin may be produced semi-synthetically starting from 1-N-(L-4-amino-2-hydroxybutyryl)-dibekacin. While, 1-N-(L-4-amino-2-hydroxybutyryl)-6″-deoxydibekacin and 1-N-(L-4-amino-2-hydroxybutyryl)-4″,6″-dideoxydibekacin may also be produced semi-synthetically using 6″-deoxydibekacin and 4″,6″-dideoxydibekacin, respectively, as the starting material.

According to a fourth aspect of this invention, there is provided a process for the production of 6″-deoxydibekacin or 4″,6″-dideoxydibekacin of the general formula (I)

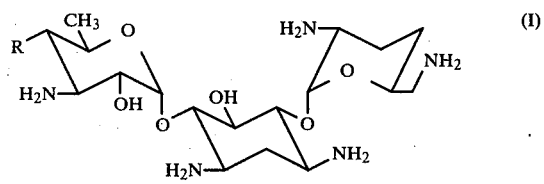

wherein R is a hydroxyl group or a hydrogen atom (R is a hydroxyl group in respect of 6″-deoxydibekacin while R is a hydrogen atom in respect of 4″,6″-dideoxydibekacin), which comprises:-

(a) protecting with a known amino-protecting group the five amino groups of dibekacin of the formula (III)

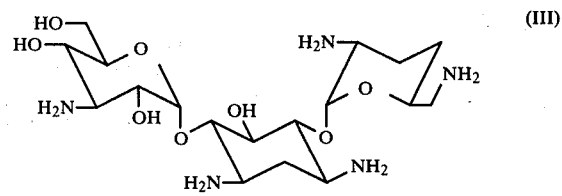

in a known manner to produce an amino-protected dibekacin derivative of the formula (III')

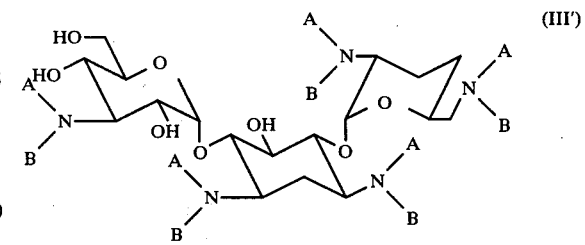

wherein A is a hydrogen atom and B is a mono-valent amino-protecting group, or A and B taken together form a di-valent amino-protecting group, (b) protecting with a known di-valent hydroxyl-protecting group simultaneously the 4″- and 6″-hydroxyl groups of the amino-protected dibekacin derivative (III') in a known manner to produce a protected derivative of the formula (III")

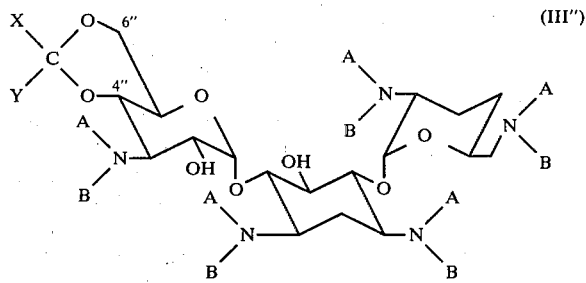 (III")

wherein A and B have the same meanings as defined above and a group of the formula

is a di-valent hydroxyl-protecting group where X and Y are hydrogen atoms both (i.e. methylene group), alkyl groups both (alkylidene group, particularly an isopropylidene group), each a hydrogen atom and an alkyl group, particularly an alkyl group of 1~6 carbon atoms (alkylidene group), an aryl group, particularly a phenyl group (benzylidene group), or an alkoxy group (alkoxymethylene group), or alternatively the group of the formula

is a cycloalkylidene group, particularly a cyclohexylidene group, (c) protecting with a known mono-valent hydroxyl-protecting group either the 2"-hydroxyl group alone or both the 5- and 2"-hydroxyl groups of said protected derivative (III") in a known manner to produce an amino-protected and hydroxyl-protected dibekacin compound of the formula (IV)

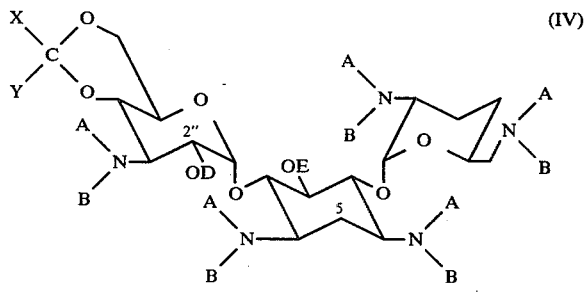 (IV)

wherein A, B and the group of the formula

have the same meanings as defined above, D is a monovalent hydroxyl-protecting group in the form of an acyl group, particularly an alkanoyl such as acetyl or an aroyl such as benzoyl, and E is a hydrogen atom or a mono-valent hydroxyl-protecting group in the form of an acyl group which may be the same as or different from the group D, (d) removing the group of protecting simultaneously the 4"- and 6"-hydroxyl groups of said protected dibekacin compound (IV) therefrom in a known manner to produce a partially protected dibekacin compound of the formula (V)

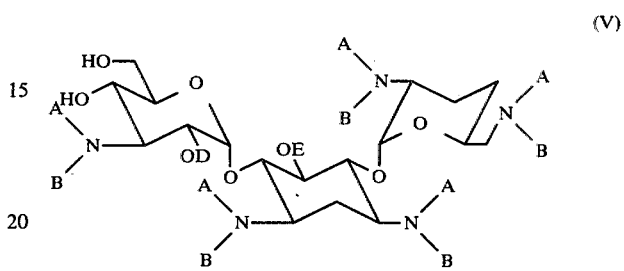 (V)

wherein A, B, D and E have the same meanings as defined above, (e) sulfonylating with a sulfonylating agent the 6"-hydroxyl group alone or simultaneously both the 4"- and 6"-hydroxyl groups of said partially protected dibekacin compound (V) in a known manner to produce a monosulfonylated or di-sulfonylated derivative of the formula (V')

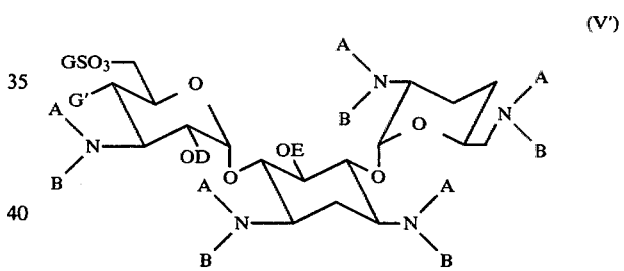 (V')

wherein A, B, D and E have the same meanings as defined above, G is a lower alkyl group of 1~4 carbon atoms, particularly methyl or ethyl, an aryl group such as phenyl group or p-methylphenyl group, or an aralkyl group, particularly a phenyl-lower alkyl group such as benzyl group, and G' is a hydroxyl group or is the same as the group $GSO_3$— shown in the formula (V').

(f) reacting the 6"-mono-sulfonylated or 4",6"-di-sulfonylated derivative (V') with an alkali metal iodide or bromide in a known manner to replace the 6"-sulfonyloxy group or the 4"- and 6"-sulfonyloxy groups by iodo or bromo group, respectively, and thereby to produce the corresponding 6"-mono-iodo or bromo derivative or the corresponding 4",6"-di-iodo or bromo derivative, (g) reducing said 6"-mono-iodo or bromo derivative or said 4",6"-di-iodo or bromo derivative with hydrogen in the presence of a hydrogenolysis catalyst to effect the dehalogenation and thereby to produce a corresponding 6"-mono-deoxy derivative (which is corresponding to such a compound of the formula (V') but where the group $GSO_3$— has been converted into a hydrogen atom and G' is remaining as the hydroxyl group) or the corresponding 4",6"-dideoxy derivative (which is corresponding to such a compound of the formula (V') but where the group GSO₃— and the group G' each have been converted into a hydrogen atom) represented by the formula (V")

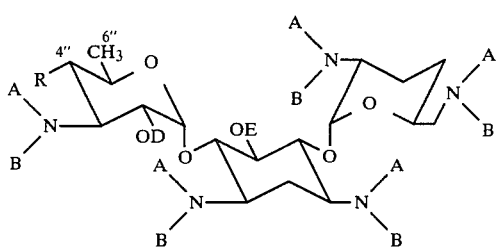

(V")

wherein A, B, D and E are as defined above, and R is a hydroxyl group or a hydrogen atom, and (h) removing the remaining amino-protecting groups and the remaining hydroxyl-protecting groups from the 6"-mono-deoxy-derivative or 4",6"-di-deoxy derivative (V") in a known manner to produce 6"-deoxydibekacin or 4",6"-dideoxydibekacin (I).

The process of the above-mentioned fourth aspect of this invention may, if necessary, include a further step of converting 6"-deoxydibekacin or 4",6"-dideoxydibekacin into a pharmaceutically acceptable acid addition salt thereof by reacting with a pharmaceutically acceptable inorganic or organic acid in a known manner.

The procedures for carrying out the process for the production of 6"-deoxydibekacin or 4",6"-dideoxydibekacin are now described.

In the first step (a) of the present process, the five amino groups of the starting dibekacin (III) are protected with a known amino-protecting group in a known manner.

The amino-protecting group available for the protection of the amino groups of dibekacin may be any known amino-protecting group which is ordinarily used in the conventional synthesis of peptides. However, the amino-protecting group employed must be of the nature that it is removable readily by such a procedure and under such reaction conditions which will substantially not break the glycoside linkage of dibekacin when the removal of the amino-protecting groups is effected from the amino-protected 6"-deoxydibekacin or 4",6"-dideoxydibekacin as produced in the process of this invention. Suitable examples of the mono-valent amino-protecting group which are available (as the group B) for the above purpose include an alkoxycarbonyl group of 2~6 carbon atoms such as tert-butoxycarbonyl and tert-amyloxycarbonyl; a cycloalkyloxycarbonyl group of 3~7 carbon atoms such as cyclohexyloxycarbonyl; an aralkyloxycarbonyl group such as benzyloxycarbonyl and p-methoxybenzyloxycarbonyl; and a substituted alkanoyl group of 2~5 carbon atoms such as trifluoroacetyl and o-nitrophenoxyacetyl. Preferred examples of the di-valent amino-protecting group available (as the groups A and B taken together) for the above-mentioned purpose include phthaloyl group and a group of Schiff base type such as salicylidene. The introduction of the amino-protecting group into dibekacin may be achieved by reacting the latter with an appropriate reagent for the introduction of the amino-protecting group which is in the form of an acid halide, acid azide, active ester or acid anhydride, in the same manner as described e.g. in the specifications of U.S. Pat. Nos. 3,929,762 and 3,939,143 as well as U.K. Pat. No. 1,426,908.

In the second step (b) of the present process, the 4"- and 6"-hydroxyl groups of dibekacin are protected simultaneously as a preliminary step for blocking the 2"-hydroxyl group occasionally together with the 5-hydroxyl group of dibekacin.

As the di-valent hydroxyl-protecting group for protecting simultaneously both the 4"- and 6"-hydroxyl groups of dibekacin, there may be employed such a protective group which is frequently used for blocking the hydroxyl groups of 1,3-glycol conventionally in the chemistry of sugars. Suitable examples of the di-valent hydroxyl-protecting group

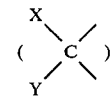

include an alkylidene group such as methylene, ethylidene and isopropylidene; an aralkylidene group such as benzylidene (when the alkylidene or aralkylidene group is used for this purpose, the 4"- and 6"-hydroxyl groups are blocked by being converted into the form of an acetal); a cycloalkylidene group such as cyclohexylidene and tetrahydro-4-pyranylidene (when the cycloalkylidene group is used for this purpose, the 4"- and 6"-hydroxyl groups are blocked by being converted into the form of a ketal); a lower alkoxy-alkylidene groups such as alkoxy-methylene, particularly methoxy-methylene (when the alkoxy-alkylidene group is employed for this purpose, the 4"- and 6"-hydroxyl groups are blocked by being converted into the form of a cyclic ortho-ester) and the like. In order to introduce the above di-valent hydroxyl-protecting group into the 4"- and 6"-hydroxyl groups of the N-protected dibekacin derivative (III'), the latter is reacted with an appropriate aldehyde or ketone in a known manner in the presence of an acid catalyst by exchange reaction with an acetal or a ketal or an orthoformate. The N-protected dibekacin derivative (III') may preferably be reacted with formaldehyde or 2,2-dimethoxypropane for the alkylidenation; with benzaldehyde for the aralkylidenation; with 1,1-dimethoxycyclohexane for the cycloalkylidenation; or with trimethyl orthoformate for the alkoxy-alkylidenation at a temperature of e.g. 10°~80° C. in the presence of an acid catalyst such as p-toluenesulfonic acid or sulfuric acid in a known manner as described in U.S. Pat. No. 3,929,762. The above protection of the 4"- and 6"-hydroxyl groups of the N-protected didekacin derivative (III') gives the 4",6"-O-protected dibekacin derivative (III") containing the two hydroxyl groups which remain in the free state at the 5- and 2"-positions.

In the third step (c) of the present process, the 2"-hydroxyl group, occasionally together with the 5-hydroxyl group of dibekacin, is protected in a known manner. As the available hydroxyl-protective groups (D,E) for blocking both the 5- and 2"-hydroxyl groups or the 2"-hydroxyl group alone, there may be mentioned a mono-valent hydroxyl-protecting group which is an acyl group, particularly a lower alkanoyl group such as acetyl; or an aroyl group such as benzoyl. For the introduction of the mono-valent hydroxyl-protecting group (D,E), the 4",6"-O-protected dibekacin derivative (III") is acylated by reacting with an acid anhydride, acid halide or active ester of the acid which is containing the acyl group to be introduced into both the 5- and 2"-hydroxyl groups or into the 2"-hydroxyl group of the dibekacin compound. The acylation may readily be achieved in a known manner. This acylation usually gives a larger proportion of the 2"-mono-O-acyl derivative and a minor proportion of the 5,2"-di-O-acyl derivative owing to that the 5-hydroxyl group is generally less reactive than the 2"-hydroxyl group. The 5,2"-di-O-acyl derivative as well as the 2"-mono-O-acyl derivative of the formula (IV) may equally be utilized in the next step (d) of the present process.

In this way, the third step (c) of the present process affords the amino-protected and hydroxyl-protected dibekacin compound (IV), and this compound is then subjected to the selective removal of the di-valent hydroxyl-protecting group

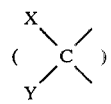

from the 4"- and 6"-hydroxyl groups therefrom. The reaction for selectively removing the di-valent hydroxyl-protecting group may readily proceed by subjecting the dibekacin compound (IV) to hydrolysis under weakly acidic conditions in the presence of a weak acid such as aqueous acetic acid or diluted hydrochloric acid, giving the partially protected dibekacin compound (V) which is an important intermediate useful in this invention. This acid hydrolysis may usually be effected at a temperature of 20° C. to 100° C.

The partially protected dibekacin compound (V) so obtained is containing the liberated 4"- and 6"-hydroxyl groups. In order to achieve the production of 6"-deoxydibekacin or 4",6"-dideoxydibekacin according to this invention, it is necessary to effect the removal of the 6"-hydroxyl group (for the 6"-deoxygenation) or the removal of both the 4"- and 6"-hydroxyl groups from the partially protected dibekacin compound (V) (for the 4",6"-dideoxygenation). For this mono-deoxygenation or di-deoxygenation, the following steps are followed in the process of the fourth aspect of this invention.

Thus, in the sulfonylation step (e) of the process of the fourth aspect invention, the 6"-hydroxyl group or the 6"- and 4"-hydroxyl groups of the partially protected dibekacin compound (V) is or are alkylsulfonylated, arylsulfonylated or aralkylsulfonylated by reacting with a sulfonylating agent of the formula

GSO₂—X wherein G is the lower alkyl group, the aryl group or the aralkyl group as defined hereinbefore and X is chlorine or bromine atom, in the reaction medium consisting of eg. dry pyridine. The sulfonylating agent GSO₂—X may be an alkylsulfonylating agent such as methanesulfonyl chloride; an arylsulfonylating agent such as p-toluenesulfonyl chloride or an aralkylsulfonylating agent such as benzylsulfonyl chloride or bromide. This sulfonylating step (e) gives the mono-sulfonylated product of which the 6"-hydroxyl group alone has been sulfonylated, and/or the di-sulfonylated product of which the 4"- and 6"-hydroxyl groups both have been sulfonylated. When the compound (V) is reacted with p-toluenesulfonyl chloride (in a substantially equimolar proportion) at ambient temperature, the 6"-mono-O-tosylated product (corresponding to the compound of the formula (V') where the group GSO₃— is tosyloxy group p—CH₃C₆H₄SO₃— and the group G' is the hydroxyl group) is produced as the main product in particular. On the other hand, when the compound (V) is reacted with methanesulfonyl chloride in a substantially 2 molar proportions or more at ambient temperature, the 4",6"-di-O-mesylated product (corresponding to the compound of the formula (V') where the group GSO₃— and the group G' both are the mesyloxy group CH₃SO₃—) is produced in a favorable yield. These 6"-mono-O-tosylated product and 4",6"-di-O-mesylated product both are the intermediate useful in this invention. Generally, the sulfonylation of the 4"- and 6"-hydroxyl groups in the above step (e) may be effected at a temperature of −10° to 100° C. and most preferably at ambient temperature or at a temperature of 10° to 60° C. and for a reaction time of 30 minutes to 1 day.

The reaction mixture from the above sulfonylation step (e) is then admixed with a small volume of water to decompose the residual amount of the unreacted sulfonylation agent, followed by concentration to dryness under reduced pressure to give a crude residue comprising the sulfonylation products. This residue is dissolved in a volume of chloroform, and the resulting solution is washed with an aqueous potassium hydrogen sulfate, with aqueous saturated sodium hydrogen carbonate and with water. The chloroform phase is then dried with anhydrous sodium sulfate and then concentrated to dryness under reduced pressure to give a crude powder comprising the sulfonylation products. When this crude powder is subjected to a column chromatography on silica gel developed with a mixture of chloroform-ethanol, the 6"-mono-O-sulfonylated product and the 4",6"-di-O-sulfonylated product may be obtained separately.

In the next step (f) of the present process, the 6"-mono-O-sulfonylated product or the 4",6"-di-O-sulfonylated product of the formula (V') is reacted with an alkali metal iodide such as sodium iodide or an alkali metal bromide such as sodium bromide in an inert organic solvent such as dry dimethylformamide, dimethylsulfoxide, acetone, dioxane and the like. The reaction may properly be effected at a reaction temperature of 50° to 150° C. and for a reaction time of 10 minutes to 1 day. By this reaction, the 6"-mono-O-sulfonylated product is iodinated or brominated to give the 6"-mono-iodo or bromo derivative or the 4",6"-di-iodo or bromo derivative.

In the further step (g) of the present process, the 6"-mono-halo derivative or the 4",6"-di-halo derivative obtained as above is reduced with hydrogen in a known manner in the presence of a hydrogenolysis catalyst such as Raney nickel, palladium, platinum and the like and in solution in an inert organic solvent such as dioxane, methanol and the like to effect the de-iodination or de-bromination. This de-iodination or de-bromination by hydrogenolysis may properly be effected at a temperature of from ambient temperature to 100° C. and for a reaction time of 30 minutes to 24 hours under atmospheric pressure or even under an elevated pressure of 10 kg/cm². This dehalogenation step (g) affords the 6"-mono-deoxy derivative or the 4",6"-dideoxy derivative of the formula (V"). In this way, the 6"-deoxygenation or the 4",6"-dideoxygenation has been achieved.

In the last step (h) of the present process, the 6"-deoxy derivative or the 4",6"-di-deoxy derivative (V") obtained in the above step (g) is subjected to the treatment for removal of the residual protective groups according to the conventional deprotecting technique. The acyl group which is present as the mono-valent hydroxyl-protecting group (D,E) may readily be removed by alkaline hydrolysis at ambient temperature, for example, by treating with 12% ammonia-methanol. When the amino-protecting group (B) is an aralkyloxycarbonyl group, this type of the amino-protecting group is removed concurrently in the catalytic reduction step (g) of the present process. When the amino-protecting group (B) is of the kind other than the aralkyloxycarbonyl group, the removal of such amino-protecting group may easily be conducted in a known manner, for example, by hydrolysis with a weak acid such as aqueous acetic acid. In this way, the desired product, that is, 6''-deoxydibekacin (when R is hydroxyl group in the formula (I)) or 4'',6''-dideoxydibekacin (when R is a hydrogen atom in the formula (I)).

Purification of 6''-deoxydibekacin or 4'',6''-dideoxydibekacin so obtained may preferably be conducted by column chromatography on an cation-exchange resin containing carboxylic functions. To this end, it is recommendable to make the chromatographic purification by adsorption on Amberlite IRC-50 or CG—50 (NH4 form or a mixture of NH4 form and H form) (a product of Rohm & Haas Co., U.S.A.) followed by elution with a dilute aqueous ammonia.

The new compound of the formula (II) according to the aforesaid second aspect of this invention includes 1-N-(L-4-amino-2-hydroxybutyryl)-6''-deoxydibekacin and 1-N-(L-4-amino-2-hydroxybutyryl)-4'',6''-dideoxydibekacin. These particular new compounds may be produced by acylation of the 1-amino group of 6''-deoxydibekacin or 4'',6''-dideoxydibekacin with L-4-amino-2-hydroxylbutyryl group.

According to the fifth aspect of this invention, therefore, there is provided a process for the production of 1-N-(L-4-amino-2-hydroxybutyryl)-6''-deoxydibekacin or 1-N-(L-4-amino-2-hydroxybutyryl)-4'',6''-dideoxydibekacin of the formula (II)

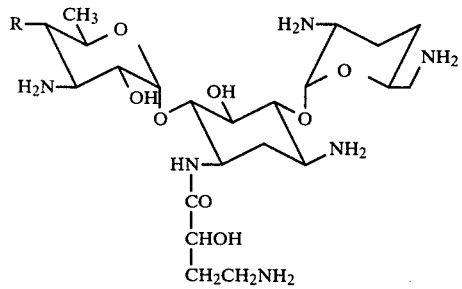

wherein R is a hydroxyl group or a hydrogen atom, which comprises (a) acylating the 1-amino group of 6''-deoxydibekacin or 4'',6''-dideoxydibekacin or a partially amino-protected derivative thereof represented by the formula (IX)

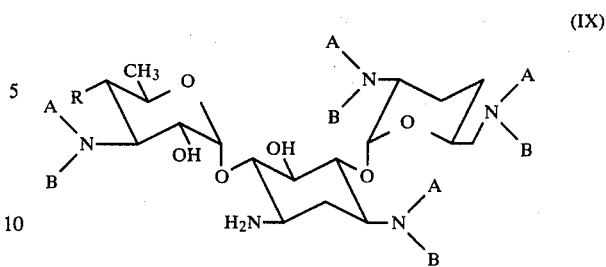

wherein R is a hydroxyl group or a hydrogen atom, and A is a hydrogen atom and at least one B is a mono-valent amino-protecting group but the other B(s) is or are each a hydrogen atom, or at least one pair of A and B taken together form a di-valent amino-protecting group but the other A and B are each a hydrogen atom, and the amino-protecting groups represented by A and B may be equal to each other or different from each other, by reaction with an amino-protected derivative of L-4-amino-2-hydroxybutyric acid or a functional equivalent thereto, to produce a 1-N-acylated product of 6''-deoxydibekacin or 4'',6''-dideoxydibekacin represented by the formula (X)

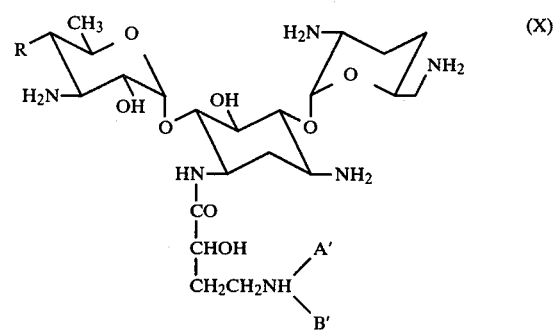

wherein A' is a hydrogen atom and B' is a hydrogen atom or a mono-valent amino-protecting group, or A' and B' taken together form a di-valent amino-protecting group, or to produce an amino-protected 1-N-acylated product of 6''-deoxydibekacin or 4'',6''-dideoxydibekacin represented by the formula (X')

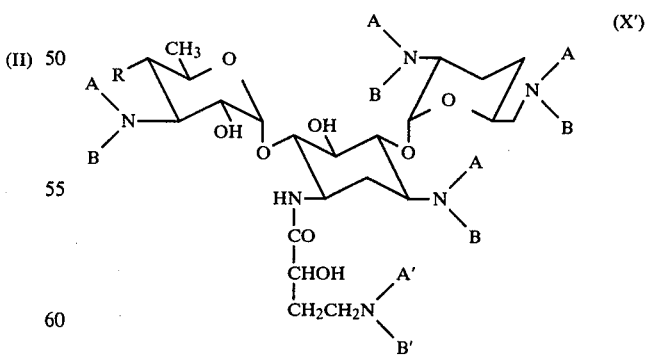

wherein R, A, B, A' and B' are as defined in the above formula (IX) or (X), and (b) removing the remaining amino-protecting group(s) from the 1-N-acylated product of the formula (X) or (X') in a known manner, to produce the compound of the formula (II).

The process of the fifth aspect of this invention may include a further step of converting the compound (II) into a pharmaceutically acceptable acid addition salt thereof by reacting with a pharmaceutically acceptable inorganic or organic acid in a known manner, if desired.

The procedures for carrying out the process of the fifth aspect of this invention are now described in more detail.

In carrying out the present process, it is possible to employ as the starting material 6"-deoxydibekacin or 4",6"-dideoxydibekacin (I) of which amino groups are not protected at all, in the form of the free acid or in the form of an acid addition salt with an appropriate acid such as hydrochloric acid or sulfuric acid. However, it is preferable to employ as the starting material such a partially amino-protected derivative of 6"-deoxydibekacin or 4",6"-dideoxydibekacin according to the formula (IX) in which all or some of the amino groups other than the 1-amino group have been protected with known amino-protecting group(s) and which may be prepared by introduction of a known amino-protecting group into the compound of the formula (I) by means of a known amino-protecting technique previously adopted in the synthesis of some known deoxy derivatives of kanamycin B. For the preparation of the partially amino-protected 6"-deoxydibekacin or 4",6"-dideoxydibekacin derivative of the formula (IX), it is feasible to utilize the amino-protecting techniques which were employed, for instance, in the preparation of the 6'-N-benzyloxycarbonyl derivative of kanamycin B as described in the specification of U.S. Pat. No. 3,781,268 or U.S. Pat. No. 3,929,762; the preparation of 2',6'-di-N-tert-butoxycarbonyl-kanamycin B or 6'-N-benzyloxycarbonyl-kanamycin B, or the mono-N- or di-N-tert-butoxycarbonyl and even tri-N-tert-butoxycarbonyl derivative of 6'-N-benzyloxycarbonyl-kanamycin B, either isolated or in mixture thereof, as described in the specification of U.K. Pat. No. 1,426,908 or U.S. Pat. No. 3,939,143; or the preparation of 2',3",6'-tetra-N-formyl derivative of kanamycin B as described in the specification of Belgian Pat. No. 817,546.

In general, suitable examples of the amino-protecting group which may be used for the protection of some amino groups of the compound of the general formula (I) as the initial material or may be present in the partially amino-protected 6"-deoxydibekacin or 4",6"-dideoxydibekacin derivative of the formula (IX) may be an ordinary amino-protecting group, including an alkoxycarbonyl group such as tert-butoxycarbonyl and tert-amyloxycarbonyl; a cycloalkyloxycarbonyl group such as cyclohexyloxycarbonyl; an aralkyloxycarbonyl group such as benzyloxycarbonyl; an acyl group such as trifluoroacetyl and o-nitrophenoxyacetyl; a phosphinothioyl group such as diphenylphosphinothioyl and dimethylphosphinothioyl; a phosphinyl group such as diphenylphosphinyl, and the like. Preferred examples of the di-valent amino-protecting group include phthaloyl group and a group of Schiff base type such as salicylidene. The introduction of the amino-protecting group of these kinds may be conducted by reacting the compound of the formula (I) with an appropriate known reagent for introduction of the amino-protecting group which may be in the form of an acid halide, acid azide, active ester or acid anhydride and the like, in the manner known in the conventional synthesis of peptides. By chosing the quantity of the reagent for introduction of the amino-protecting group employed in a proportion of 0.5 to 6 mol. per mol. of the compound of the formula (I), it is possible to prepare a mixture of different, partially amino-protected derivatives (IX) at any ratio, due to the difference in the reactivity of the respective amino groups of the compound (I).

In the process of the fifth aspect of this invention, it is practical to employ as the starting material such an amino-protected 6"-deoxydibekacin or 4",6"-dideoxydibekacin derivative in which all or some of the amino groups other than the 1-amino group have or has been blocked, for example, a 3,2',6',3"-tetra-N-protected derivative, a 3,2',6'-tri-N-protected derivative, a 2',6',3"-tri-N-protected derivative, a 2',6'-di-N-protected derivative and a 6'-mono-N-protected derivative. Besides, a mixture of two or more of these partially N-protected derivatives may, without being purified, be used for the 1-N-acylation step of the present process.

In order to ensure that the desired product of the general formula (II) can be produced in a high yield in accordance with the process of the fifth aspect invention, it needs only that just the 1-amino group of 6"-deoxydibekacin or 4",6"-dideoxydibekacin is selectively acylated with L-4-amino-2-hydroxybutyric acid. Accordingly, it will be evident that most preferably, a 3,2',6',3"-tetra-N-protected derivative of the compound (I), that is, the amino-protected derivative of the compound (I) in which all the amino groups other than the 1-amino group have been blocked with the protective groups is employed as the starting material to be 1-N-acylated in the present process.

To prepare the 3,2',6',3"-tetra-N-protected derivative of the formula (IX) from the compound of the formula (I), the following procedure may be used, for instance. Thus, there can be applied a known method of U.S. Pat. No. 4,136,254 of Nagabhushan et al by which a 3,2',6'-tri-N-acylated protected derivative of kanamycin B is prepared by reacting kanamycin B with a di-valent transition metal cation, for example, cation of copper (II), nickel (II), cobalt (II) etc. for the formation of a metal complex of kanamycin B, reacting this kanamycin B-metal complex with an acylation agent known as the amino-protecting group-introducing reagent for the protection of all the amino groups other than the 1-amino and 3"-amino groups of the kanamycin B moiety of the kanamycin B-metal complex (said 1- and 3"-amino groups having been blocked by complexing with the di-valent metal cation in the kanamycin B-metal complex), and then removing the di-valent metal cation from said complex, e.g., by treatment with hydrogen sulfide or by treatment with aqueous ammonia. Or, there can be applied a method of our copending Japanese patent application No. 138402/78 (corresponding to our co-pending U.S. patent application No. 090,591; co-pending U.K. patent application No. 7938894; Belgian Pat. No. 879,925) by which a 3,2',6'-tri-N-acylated protected derivative of kanamycin B is prepared in a similar way to the aforesaid known method of Nagabhushan et al except that zinc cation is employed instead of the di-valent transition metal cation. In this way, a 3,2',6'-tri-N-protected derivative of the formula (IX) can be prepared from the compound of the formula (I) in a high yield. The 3"-amino group of this 3,2',6'-tri-N-protected derivative (IX) so prepared can further be protected by the selective acylation according to a selective 3"-N-acylation method of our co-pending Japanese patent application No. 73064/79 (see claim 15 of said Belgian Pat. No. 879,923) for the production of an amino-protected derivative of an aminoglycosidic antibiotic of which all the amino groups other than the 1-amino group have been protected selectively, so that a 3,2',6',3''-tetra-N-protected derivative of the compound (I) can be prepared in a high yield. In accordance with the selective 3''-N-acylation method of the co-pending Japanese patent application No. 73064/79 (as described in the claim 15 of the Belgian Pat. No. 879,923), the above-mentioned 3,2',6'-tri-N-protected derivative of the compound (I) is reacted with a formic acid alkyl ester, a di-halo- or tri-haloalkanoic acid alkyl ester, formylimidazole or an N-alkanoylimidazole as the acylation agent, whereby the 3''-amino group can be acylated selectively with the acyl residue of the acylation agent employed in a high yield, without involving the acylation of the 1-amino group of said 3,2',6'-tri-N-protected derivative. The 3,2',6',3''-tetra-N-acylated derivative, for example, 3,2',6'-tri-N-benzyloxycarbonyl-3''-N-trifluoroacetyl derivative, of 6''-deoxydibekacin or 4'',6''-dideoxydibekacin which may be obtained by applying the above-mentioned methods of the U.S. Pat. No. 4,136,254 and of the Belgian Pat. No. 879,923 is a most preferred material to be 1-N-acylated selectively with the L-4-amino-2-hydroxybutyric acid in the 1-N-acylation step of the present process.

In the process of this fifth aspect invention, the 1-amino group of the compound of the formula (I) or the 1-amino group of the partially amino-protected derivatives (IX) thereof, either isolated or in mixture of two or more of them, is acylated with L-4-amino-2-hydroxybutyric acid of which the amino group is not protected or has been protected. This 1-N-acylation may be conducted according to any of the conventional methods for the synthesis of peptides, for instance, according to the known dicyclohexylcarbodiimide method, the known mixed acid anhydride method, the known azide method or the active ester method and the like, using L-4-amino-2-hydroxybutyric acid as such or in the form of its reactive derivative (as the functional equivalent thereof). As the amino-protecting group for protection of the amino group of L-4-amino-2-hydroxybutyric acid may be employed such an amino-protecting group which is the same as or different from the one present in the compound (IX). Particularly, a preferred amino-protecting group for this purpose is tert-butoxycarbonyl group which is easily removable by treatment with aqueous trifluoroacetic acid or acetic acid or with diluted aqueous hydrochloric acid. Benzyloxycarbonyl group which is removable by a conventional hydrogenolysis in the presence of a catalyst such as palladium or platinum oxide is a convenient N-protecting group.

The 1-N-acylation in the present process may preferably be carried out in an aqueous organic solvent according to the active ester method using L-4-amino-2-hydroxybutyric acid in the form of its active ester. For example, N-hydroxysuccinimide ester of L-4-benzyloxycarbonylamino-2-hydroxybutyric acid may preferably be used as the active ester which may be prepared by a conventional method of preparing the active ester. This active ester preferably may be used in a proportion of from 0.5 to 3 molar equivalents and preferably of from 1 to 1.5 molar equivalents per mol of the 6''-deoxydibekacin or 4'',6''-dideoxydibekacin compound to be 1-N-acylated. The aqueous organic solvent used in the reaction medium may be a water-miscible organic solvent such as dioxane, 1,2-dimethoxyethane, dimethylformamide, tetrahydrofuran, and the like. The 1-N-acylation may be effected at ambient temperature or, if desired, at an elevated temperature of 20°~90° C. and for a reaction time of several hours and preferably of 5~6 hours.

When the 1-N-acylation in the present process is conducted using as the starting material such a partially amino-protected derivative in which some, but not all, of the amino groups other than the 1-amino group has or have been protected, for example, the 6'-N-protected derivative of 6''-deoxydibekacin or 4'',6''-dideoxydibekacin, the acylation products as formed may partially be purified by a column chromatography, for example, on silica gel so that the unreacted starting material is removed, giving a mixture of the desired 1-N-mono-acylated product with the otherwise N-acylated products, as the case be in the synthesis of 1-N-(L-4-amino-2-hydroxybutyryl)-3',4'-dideoxykanamycin B as described in the specification of U.S. Pat. No. 4,107,424. These mixed acylation products may, without being purified and/or isolated, be subjected immediately to the subsequent de-protecting step of the present process, followed by the purification and isolation so that the desired 1-N-mono-acylated product is obtained.

In the second step of the process of this fifth aspect invention, the 1-N-acylation product (including the mixed acylation products) as obtained in the 1-N-acylation step of the present process is subjected to the removal of the amino-protecting groups, if these are still remaining in the 1-N-acylation product. The removal of the protecting groups is effected by a conventional deprotecting technique. Thus, the amino-protecting group of the alkoxycarbonyl type is removed by weak acid hydrolysis using an aqueous solution of trifluoroacetic acid or acetic acid and the like or a diluted aqueous solution of an inorganic acid such as hydrochloric acid. The aralkyloxycarbonyl group such as benzyloxycarbonyl may be removed by an ordinary catalytic reduction (hydrogenolysis). When phthaloyl group is present as the amino-protecting group, it can be removed by heating in a solution of hydrazine hydrate in a lower alkanol.

The deprotected acylation product as obtained from the second, de-protecting step of the present process may contain comprise the desired 1-N-acylation product of the formula (II) together with some isomers thereof. The desired 1-N-(L-4-amino-2-hydroxybutyryl) derivative (II) may be isolated and purified chromatographically using a cation-exchanger containing carboxylic functions, such as Amberlite CG-50 (a product of Rohm & Haas Co., U.S.A.) or CM-Sephadex C-25 (a product of Pharmacia Co., Sweden) and assaying the antibacterial activity of the fractions of the eluate by means of a proper kanamycin-sensitive strain and kanamycin-resistant strain of bacteria.

Besides, the new compound of the formula (II) according to the second aspect of this invention may also be prepared starting from the known compound, 1-N-(L-4-amino-2-hydroxybutyryl)-3',4'-dideoxykanamycin B, that is, 1-N-(L-4-amino-2-hydroxybutyryl)-dibekacin. According to the sixth aspect of this invention, therefore, there is provided a process for the production of 1-N-(L-4-amino-2-hydroxybutyl)-6''-deoxydibekacin or -4'',6''-dideoxydibekacin of the formula (II)

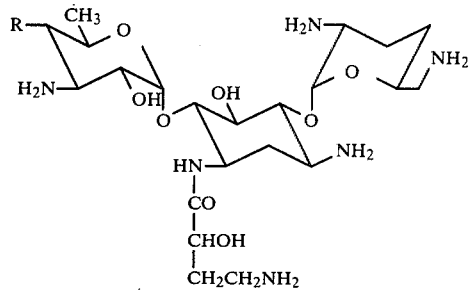

(II)

wherein R is a hydroxyl group or a hydrogen atom, which comprises (a) protecting with a known amino-protecting group the five amino groups of 1-N-(L-4-amino-2-hydroxybutyryl)-dibekacin of the formula (VI)

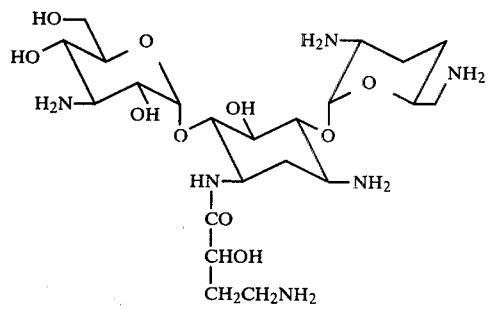

(VI)

in a known manner to produce an amino-protected derivative of the formula (VI′)

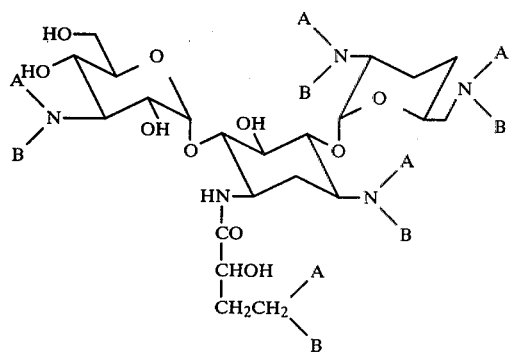

(VI′)

wherein A is a hydrogen atom and B is a mono-valent amino-protecting group, or A and B taken together form a di-valent amino-protecting group, (b) protecting with a known di-valent hydroxyl-protecting group simultaneously the 4″- and 6″-hydroxyl groups of the amino-protected derivative (VI′) in a known manner to produce a protected derivative of the formula (VI″)

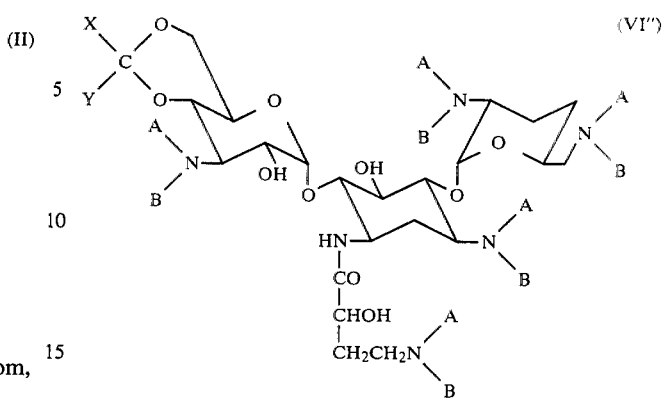

(VI″)

wherein A and B have the same meanings as defined above and the group of the formula

is a di-valent hydroxyl-protecting group where X and Y are each a hydrogen atom, an alkyl group, an aryl group, or an alkoxy group, or the group of the formula

is a cycloalkylidene group, (c) protecting with a known mono-valent hydroxyl-protecting group either the two, 2″- and 2‴-hydroxyl groups or the three, 5-, 2″- and 2‴-hydroxyl groups of said protected derivative (VI″) in a known manner to produce an amino-protected and hydroxyl-protected derivative of the formula (VII)

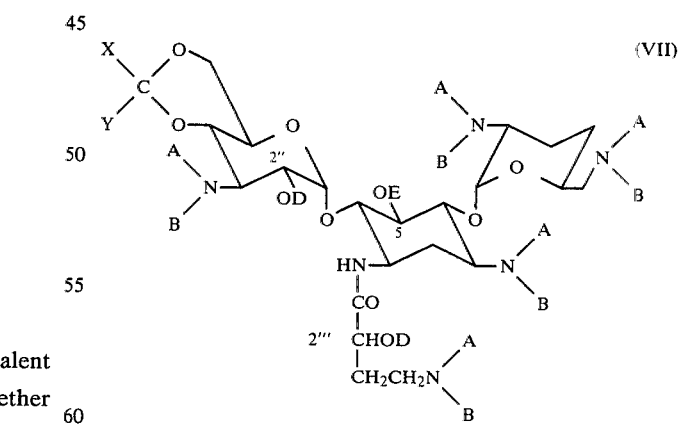

(VII)

wherein A, B and the group of the formula

have the same meanings as defined above, D is a monovalent hydroxyl-protecting group in the form of an acyl group, and E is a hydrogen atom or a mono-valent hydroxyl-protecting group in the form of an acyl group, (d) removing the group

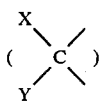

of protecting the 4''- and 6''-hydroxyl groups of said amino-protected and hydroxyl-protected derivative (VII) therefrom in a known manner to produce a partially protected compound of the formula (VIII)

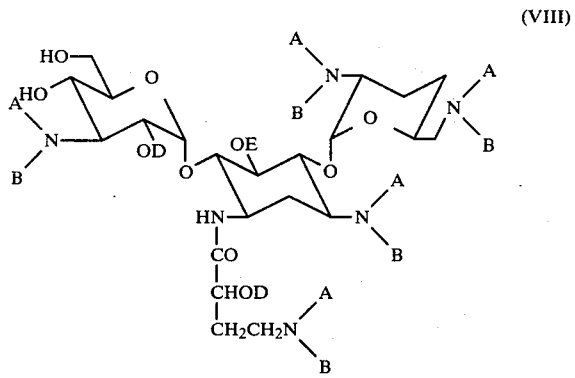

wherein A, B, D and E have the same meanings as defined above, (e) sulfonylating with a sulfonylation agent the 6''-hydroxyl group alone or simultaneously both the 4''-and 6''-hydroxyl groups of said partially protected compound (VIII) in a known manner to produce a mono-sulfonylated or di-sulfonylated derivative of the formula (VIII')

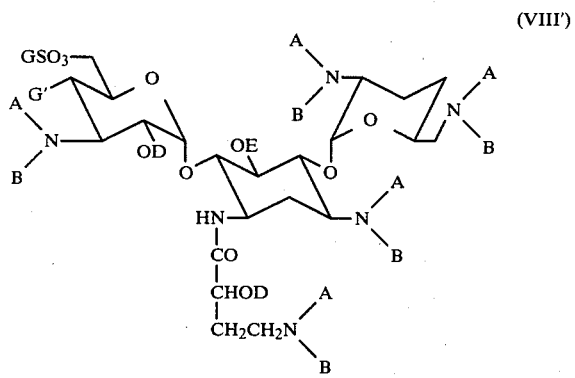

wherein A, B, D and E have the same meanings as defined above, G is a lower alkyl group of 1~4 carbon atoms, an aryl group such as phenyl or p-methylphenyl, or an aralkyl group such as benzyl, and G' is a hydroxyl group or is the same as the group $GSO_3$— shown in the formula (VIII'), (f) reacting the 6''-mono-sulfonylated or 4'',6''-disulfonylated derivative (VIII') with an alkali metal iodide or bromide in a known manner to replace the 6''-sulfonyloxy group or the 4''- and 6''-sulfonyloxy groups by iodo or bromo group, respectively, and thereby to produce the corresponding 6''-mono-iodo or bromo derivative or the corresponding 4'',6''-di-iodo or bromo derivative, (g) reducing said 6''-mono-iodo or bromo derivative or said 4'',6''-di-iodo or bromo derivative with hydrogen in the presence of a hydrogenolysis catalyst to effect the dehalogenation and thereby to produce the corresponding 6''-mono-deoxy derivative (which is corresponding to such a compound of the formula (VIII') but where the group $GSO_3$— has been converted into a hydrogen atom and G' is remaining as the hydroxyl group) or the corresponding 4'',6''-dideoxy derivative (which is corresponding to such a compound of the formula (VIII') but where the group $GSO_3$— and the Group G' each have been converted into a hydrogen atom) represented by the formula (VIII'')

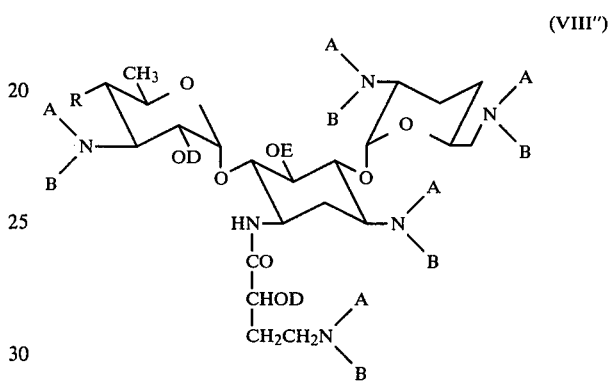

wherein A, B, D and E are as defined above and R is a hydroxyl group or a hydrogen atom, and (h) removing the remaining amino-protecting groups and the remaining hydroxyl-protecting groups from the 6''-mono-deoxy derivative or 4'',6''-di-deoxy derivative (VIII'') in a known manner to produce 1-N-(L-4-amino-2-hydroxybutyryl)-6''-deoxy or -4'',6''-dideoxydibekacin of the formula (II).

The process of the above-mentioned sixth aspect of this invention may, if necessary, include a further step of converting the compound of the formula (II) into a pharmaceutically acceptable acid addition salt thereof by reacting with a pharmaceutically acceptable inorganic or organic acid in a known manner.

The steps (a) to (h) of the process of the sixth aspect invention may be carried out in the same manner as hereinbefore described in respect of the steps (a) to (h) of the process of the aforesaid fourth aspect invention, respectively. Accordingly, the descriptions of the procedures for carrying out the respective steps of the process of the sixth aspect invention are omitted here.

This invention is now illustrated with reference to the following Examples to which this invention is not limited. Examples 1 and 2 are illustrative of the first and fourth aspects of this invention, Examples 4 and 5 are illustrative of the second and fifth aspects of this invention, and Example 3 is illustrative of the sixth aspect of this invention.

EXAMPLE 1

(a) Synthesis of 2''-O-benzoyl-1,3,2',6',3''-penta-N-tert-butoxycarbonyl-dibekacin Dibekacin (3.0 g, 6.65 m mol) was dissolved in 10 ml of water, and the resulting solution was admixed with 4.63 ml (33.24 m mol) of triethylamine and 30 ml of methanol. To the admixture was dropwise added a solution of 11.5 g (50 m mol) of tert-butyl S-4,6-dimethylpyrimid-2-ylthiocarbonate in 20 ml of methanol, followed by stirring at 60° C. for 5 hours to effect the reaction of introducing the tert-butoxycarbonyl group as the N-protecting group into the starting dibekacin. The reaction solution was concentrated under reduced pressure to about a half volume and then poured into 650 ml of water, followed by standing overnight in a refrigerator. The precipitate formed was removed by filtration and washed with 300 ml of water and with 150 ml of ethyl ether to give 4.73 g (yield 75%) of a faintly brown powder of 1,3,2',6',3''-penta-N-tert-butoxycarbonyl-dibekacin.

This powder (1.0 g, 1.05 m mol) was dissolved in 21 ml of anhydrous dimethylformamide, and the resultant solution was further admixed with 432 mg (3 m mol) of 1,1-dimethoxycyclohexane and 42 mg (0.24 m mol) of p-toluenesulfonic acid, followed by stirring at ambient temperature for 16 hours to effect the reaction of introducing the 4'',6''-O-cyclohexylidene group. The reaction solution was admixed with 0.1 ml of triethylamine and then concentrated to dryness under reduced pressure. The residue was taken up in 100 ml of chloroform and the solution obtained was washed with the equal volume of water and dried on anhydrous sodium sulfate, followed by concentration under reduced pressure, affording 1.10 g (yield 100%) of a faintly yellow powder of 1,3,2',6',3''-penta-N-tert-butoxycarbonyl-4'',6''-O-cyclohexylidene-dibekacin.

This powder (800 mg, 0.775 m mol) was dissolved in 16 ml of dry pyridine, and the solution was admixed with 260 mg (1.86 m mol) of benzoyl chloride, followed by stirring at 60° C. overnight to effect the reaction of introducing the 2''-O-benzoyl group. The reaction solution was admixed with 1 ml of methanol to decompose the excess of the benzoyl chloride unreacted. The reaction solution was then concentrated to a smaller volume under reduced pressure to give an oil. This oil was taken up in 50 ml of chloroform, and the resulting solution was washed with the same volume of 5% aqueous potassium hydrogen sulfate, then with the same volume of saturated aqueous sodium hydrogen carbonate, and finally with the same volume of water. The solution in chloroform was separated, dehydrated on anhydrous sodium sulfate and concentrated under reduced pressure. The residue was washed with small volumes of chloroform and n-hexane, giving 826 mg (yield 94%) of a faintly yellow powder of 2''-O-benzoyl-1,3,2',6',3''-penta-N-tert-butoxycarbonyl-4'',6''-O-cyclohexylidene-dibekacin.

This powder (816 mg, 0.718 m mol) was dissolved in 20 ml of a mixture of acetic acid, methanol and water (2:1:1 by volume), and the resulting solution was stirred at 50° C. for 1 hour and at 40° C. for 3 hours to effect the hydrolytic removal of the 4'',6''-O-cyclohexylidene group. The reaction solution was concentrated under reduced pressure and the residue was taken up in 50 ml of chloroform. The solution was washed with the same volume of aqueous saturated sodium hydrogen carbonate and with the same volume of water, followed by dehydration of the chloroform phase on anhydrous sodium sulfate and concentration of the solution in chloroform to dryness under reduced pressure to give 758 mg (yield 100%) of a faintly yellow powder of 2''-O-benzoyl-1,3,2',6',3''-penta-N-tert-butoxycarbonyl-dibekacin.

(b) Synthesis of 4'',6''-dideoxydibekacin

The 2''-O-benzoyl-1,3,2',6',3''-penta-N-tert-butoxycarbonyl-dibekacin (850 mg, 0.805 m mol) obtained in the above procedure of Example 1(a) was dissolved in 20 ml of anhydrous pyridine, followed by addition of 483 mg (4.24 m mol) of mesyl chloride thereto and reaction of the resulting admixture at 40°~50° C. overnight to effect the mesylation. The reaction mixture was admixed with a small volume of water for decomposition of the unreacted mesyl chloride, followed by concentration to dryness under reduced pressure. The residue was taken up in 100 ml of chloroform and the solution obtained was washed with the same volume of 5% aqueous potassium hydrogen sulfate, with the same volume of aqueous saturated sodium hydrogen carbonate and with the same volume of water, and the chloroform phase was dehydrated on anhydrous sodium sulfate and concentrated to dryness under reduced pressure to afford a lightly brown powder of 2''-O-benzoyl-1,3,2',6',3''-penta-N-tert-butoxycarbonyl-4'',6''-di-O-mesyl-dibekacin. This crude powder was purified by a column chromatography on silica gel (100 g, Wako Gel C-100, a product of Wako Junyaku Co., Japan) developed with a mixture of chloroform and ethanol (100:1 by volume) to give 859 mg (yield 88%) of a purified colorless powder.

This colorless powder (350 mg, 0.289 m mol) was dissolved in 7 ml of anhydrous dimethylformamide, and the resulting solution was admixed with a large excess (3.5 g) of sodium iodide, followed by stirring at 95° C. for 5 hours under argon atmosphere to effect the 4'',6''-di-iodination. The reaction solution was admixed with 50 ml of water, and the precipitate formed was removed by filtration and washed with water. The precipitate collected was dissolved in 50 ml of chloroform, and the solution was washed with the same volume of 20% aqueous sodium thiosulfate and then with the same volume of water. The chloroform phase was dehydrated on anhydrous sodium sulfate and concentrated to dryness under reduced pressure, giving a colorless powder (359 mg). This powder was purified by a chromatography on thin layer of silica gel (Silica Gel DF 500, KT-plate, a product of Camag AG., Swiss) developed with a mixture of chloroform and ethanol (20:1 by volume), when the product present in the region of the silica gel thin layer corresponding to Rf 0.6 was collected. A colorless powder (210 mg, yield 57%) of 2''-O-benzoyl-1,3,2',6',3''-penta-N-tert-butoxycarbonyl-4'',6''-di-iodo-dibekacin was afforded.

This colorless powder (210 mg) was dissolved in 5 ml of dioxane, and the solution was admixed with 50 mg of Raney nickel catalyst (R-200, a product of Nikko Rika Co., Japan) and was subjected to the catalytic hydrogenolysis with hydrogen at a hydrogen pressure of 3.6 Kg/cm$^2$ in a Parr apparatus overnight at ambient temperature to effect the de-iodination. The reaction mixture was filtered to remove the catalyst therefrom, and the filtrate was concentrated to dryness under reduced pressure. The residue was dissolved in 5 ml of 12% ammonia-methanol and the solution was allowed to stand overnight to effect the debenzoylation. The reaction solution was then concentrated under reduced pressure, and the solid residue was taken up in 20 ml of chloroform, followed by washing with water. The solution in chloroform was then dried on anhydrous sodium sulfate and concentrated to dryness under reduced pressure, yielding a colorless powder. This powder was dissolved in 2 ml of a solution of 90% trifluoroacetic acid in water and then allowed to stand at ambient temperature for 45 minutes to effect the removal of the tert-butoxycarbonyl groups. The reaction solution was again concentrated under reduced pressure and the residue was washed with a volume of ethyl ether to give a faintly yellow powder (comprising the trifluoroacetate of the desired 4",6"-dideoxydibekacin). This powder was taken up in a volume of water and passed through a column of 17 ml of Amberlite CG-50 (NH$_4$+) for adsorption of the desired product. The Amberlite column was washed with water and then eluted with 0.4 M aqueous ammonia. The biologically active eluate was collected and concentrated to dryness under reduced pressure to afford 36 mg of a colorless powder of the desired 4",6"-dideoxydibekacin in the form of its sesqui-carbonate. Yield 52%. This powder decomposed slowly at about 129° C. and gave a specific optical rotation $[\alpha]_D^{23} = +126°$ (c 0.5, water).

EXAMPLE 2

Synthesis of 6"-deoxydibekacin

The 2"-O-benzoyl-1,3,2',6',3"-penta-N-tert-butoxycarbonyl-dibekacin (500 mg, 0.473 m mol) obtained in the procedure of Example 1(a) was dissolved in 10 ml of anhydrous pyridine, and the resulting solution was admixed with 130 mg (1.14 m mol) of mesyl chloride. The admixture was stirred at 30° C. overnight to effect the mesylation. The reaction solution was admixed with a small volume of water, followed by standing for 30 minutes at ambient temperature to decompose the unreacted mesyl chloride. The reaction solution was concentrated to dryness under reduced pressure, and the residue was dissolved in 50 ml of chloroform. The solution in chloroform was washed with the same volume of 5% aqueous potassium hydrogen sulfate, with the same volume of aqueous saturated sodium hydrogen carbonate and then with the same volume of water. The chloroform phase was dried on anhydrous sodium sulfate and concentrated to dryness under reduced pressure to give a lightly brown powder. This powder was purified by a column chromatography on silica gel (Wako Gel C-200, a product of Wako Junyaku Co., Japan) developed with a mixture of chloroform and ethanol (50:1 by volume) to give 114 mg (yield 20%) of a colorless powder of 2"-O-benzoyl-1,3,2',6',3"-penta-N-tert-butoxycarbonyl-4",6"-di-O-mesyldibekacin and 250 mg (yield 47%) of a colorless powder of 2"-O-benzoyl-1,3,2',6',3"-penta-N-tert-butoxycarbonyl-6"-O-mesyl-dibekacin.

The colorless powder (39 mg, 0.0344 m mol) of the latter, that is, the 6"-O-mesylated product was dissolved in 1 ml of anhydrous dimethylformamide, and the resultant solution was admixed with 390 mg (2.6 m mol) of sodium iodide, followed by agitating the admixture at 90° C. for 2 hours to effect the 6"-iodination. The reaction solution was admixed with 30 ml of chloroform, and the solution obtained was washed with three 30 ml-portions of aqueous saturated sodium chloride, with 30 ml of aqueous 20% sodium thiosulfate and then with 30 ml of water. The chloroform phase was dried on anhydrous sodium sulfate and concentrated to dryness under reduced pressure, giving 38 mg of a colorless powder of 2"-O-benzoyl-1,3,2',6',3"-penta-N-tert-butoxycarbonyl-6"-iodo-dibekacin.

This powder was dissolved in 1.5 ml of dioxane and the solution was admixed with 20 mg of Raney nickel catalyst (R-200, a product of Nikko Rika Co., Japan) and then subjected to a catalytic hydrogenolysis at a hydrogen pressure of 3.6 Kg/cm$^2$ for 24 hours in a Paar apparatus to effect the de-iodination. The reaction mixture was filtered to remove the catalyst therefrom, and the filtrate was concentrated to dryness under reduced pressure. The residue was taken up in 2 ml of a solution of 12% ammonia in methanol. The resulting solution was allowed to stand at ambient temperature overnight to effect the de-benzoylation. The reaction solution was concentrated to dryness under reduced pressure to afford a colorless powder. This powder was dissolved in 1 ml of aqueous 90% trifluoroacetic acid, followed by standing at ambient temperature for 45 minutes to effect the removal of the tert-butoxycarbonyl groups. The reaction solution was concentrated to dryness under reduced pressure, and the residue was washed with a volume of ethyl ether to give a faintly yellow powder (comprising the trifluoroacetate of the desired 6"-deoxydibekacin). This powder was dissolved in water and the aqueous solution was passed through a column of 5 ml of Amberlite CG-50 (NH$_4$+) for adsorption of the desired product. The Amberlite column was washed with water and then eluted with 0.4 M aqueous ammonia. The active eluate was collected and concentrated to dryness under reduced pressure to give 12 mg of a colorless powder of 6"-deoxydibekacin in the form of its sesqui-carbonate. The yield was amounting to 75% as calculated from the intermediate 6"-O-mesylated product mentioned hereinbefore. This 6"-deoxydibekacin sesqui-carbonate decomposed slowly at about 131° C. and gave a specific optical rotation $[\alpha]_D^{26} = +101°$ (c 0.44, water).

EXAMPLE 3

(a) Synthesis of 2",2'''-di-O-benzoyl-3,2',6',3",4'''-penta-N-tert-butoxycarbonyl-1-N-(L-4-amino-2-hydroxybutyryl)-dibekacin 1-N-(L-4-Amino-2-hydroxybutyryl)-dibekacin (679 mg., 1.23 m mol) was dissolved in 14 ml of aqueous 50% dioxane, and to the resulting solution was added 1 ml (7.2 m mol) of triethylamine and then dropwise a solution of 2.96 g (12.3 m mol) of tert-butyl S-4,6-dimethylpyrimid-2-ylthiocarbonate in 7 ml of dioxane. The admixture obtained was stirred at ambient temperature for 40 hours to effect the N-tert-butoxycarbonylation, followed by concentration of the reaction solution to dryness under reduced pressure. The residue was washed with 100 ml portions of n-hexane and water, affording 1.0 g (yield 82%) of a faintly yellow powder of 3,2',6',3",4'''-penta-N-tert-butoxycarbonyl-1-N-(L-4-amino-2-hydroxybutyryl)-dibekacin.

This powder (1.0 g., 1.01 m mol) was taken up in 20 ml of anhydrous dimethylformamide, and the solution obtained was admixed with 4 mg of p-toluenesulfonic acid and 0.5 ml (4.1 m mol) of 2,2-dimethoxypropane, followed by stirring the admixture at ambient temperature for 17 hours to effect the 4",6"-O-isopropylidenation. The reaction solution, after addition of one drop of triethylamine thereto, was concentrated to dryness under reduced pressure, and the residue was dissolved in 150 ml of chloroform. The solution in chloroform was then washed with two 100 ml portions of aqueous saturated sodium hydrogen carbonate and then with 100 ml of aqueous saturated sodium chloride, and the chloroform phase was subsequently dried on anhydrous sodium sulfate and concentrated to dryness to give 1.1 g of a lightly yellow crude powder of 3,2',6',3",4'''-penta-N-tert-butoxycarbonyl-4",6"-O-isopropylidene-1-N-(L-4-amino-2-hydroxybutyryl)-dibekacin.

This powder was dissolved in 30 ml of chloroform and purified chromatographically in a column of silica gel (100 g., Wako Gel C-200, a product of Wako Junyaku Co., Japan) developed with a mixture of chloroform and ethanol (20:1 by volume). The fractions of the eluate which contained the desired product were concentrated to dryness under reduced pressure to afford 842 mg of a purified colorless powder of the desired product (yield 77%).

This powder (840 mg, 0.78 m mol) was dissolved in 10 ml of anhydrous pyridine to which was then added 0.4 ml (3.4 m mol) of benzoyl chloride. The resulting solution was stirred at ambient temperature for 18 hours to effect the 2",2'''-di-O-benzoylation. The reaction solution was admixed with one drop of water to decompose the unreacted, excessive benzoyl chloride, and the reaction solution was then concentrated to dryness under reduced pressure. The residue was taken up in 100 ml of chloroform and the solution was washed with 100 ml of 0.25 N hydrochloric acid, with three 50 ml portions of aqueous saturated sodium hydrogen carbonate and then with 100 ml of aqueous saturated sodium chloride. The solution in chloroform was dried on anhydrous sodium sulfate and concentrated to dryness under reduced pressure to afford 1.017 g (yield 100%) of a faintly yellow powder of 2",2'''-di-O-benzoyl-3,2',6',3",4'''-penta-N-tert-butoxycarbonyl-4",6"-O-isopropylidene-1-N-(L-4-amino-2-hydroxybutyryl)-dibekacin.

This powder (975 mg, 0.76 m mol) was dissolved in 20 ml of a mixture of acetic acid, methanol and water (2:1:1 by volume) and the resulting solution was agitated at ambient temperature for 15 hours to effect the deisopropylidenation, and the reaction solution was concentrated to dryness under reduced pressure. The residue was dissolved in 100 ml of chloroform and the solution was washed with two 100 ml portions of aqueous saturated sodium hydrogen carbonate and then with 100 ml of aqueous saturated sodium chloride. The chloroform phase (the solution) was dehydrated with anhydrous sodium sulfate and then concentrated to dryness under reduced pressure to give 873 mg (yield 93%) of a faintly yellow powder of 2",2'''-di-O-benzoyl-3,2',6',3",4'''-penta-N-tert-butoxycarbonyl-1-N-(L-4-amino-2-hydroxybutyryl)-dibekacin.

(b) Synthesis of 1-N-(L-4-amino-2-hydroxybutyryl)-4",6"-dideoxydibekacin and 1-N-(L-4-amino-2-hydroxybutyryl)-6"-deoxydibekacin 2",2'''-Di-O-benzoyl-3,2',6',3",4'''-penta-N-tert-butoxycarbonyl-1-N-(L-4-amino-2-hydroxybutyryl)-dibekacin (250 mg, 0.2 m mol) obtained in the Example 3(a) was dissolved in 5 ml of anhydrous pyridine, and the resulting solution, after addition of 0.06 ml (1.3 m mol) of mesyl chloride thereto, was agitated at ambient temperature for 16 hours to effect the mesylation. To the reaction solution was added one drop of water to decompose the unreacted, excessive mesyl chloride. The reaction solution was then concentrated to dryness under reduced pressure and the residue was dissolved in 25 ml of chloroform. The solution obtained was washed with 25 ml of 0.2 N hydrochloric acid, with three 25 ml portions of aqueous saturated sodium hydrogen carbonate and then with 25 ml of aqueous saturated sodium chloride, and subsequently the solution in chloroform was dried on anhydrous sodium sulfate, followed by concentration to dryness under reduced pressure, giving 271 mg (yield 96%) of a lightly brown powder comprising 2",2'''-di-O-benzoyl-3,2',6',3",4'''-penta-N-tert-butoxycarbonyl-4",6"-di-O-mesyl-1-N-(L-4-amino-2-hydroxybutyryl)-dibekacin (which gave a single spot at Rf 0.25 in a silica gel thin layer chromatography developed with chloroform-methanol (30:1)) and a minor proportion of 2",2'''-di-O-benzoyl-3,2',6',3",4'''-penta-N-tert-butoxycarbonyl-6"-O-mesyl-1-N-(L-4-amino-2-hydroxybutyryl)-dibekacin (which gave a single spot at Rf 0.18 in the same silica gel thin layer chromatography just mentioned above).

This powder (220 mg, 0.155 m mol) was dissolved in 4.4 ml of dry dimethylformamide, and the solution was admixed with a large excess (2.3 g) of sodium iodide, followed by agitation at 90° C. for 6 hours to effect the substitutive iodination. The reaction solution was admixed with 50 ml of water and the precipitate as formed was removed by filtration. The precipitate collected was dissolved in 20 ml of chloroform and the solution was washed with two 20 ml portions of aqueous 20% sodium thiosulfate and then with 20 ml of aqueous saturated sodium chloride. The solution in chloroform was dried on anhydrous sodium sulfate and concentrated to dryness under reduced pressure to give 224 mg (yield 99%) of a colorless powder comprising a main proportion of 2",2'''-di-O-benzoyl-3,2',6',3",4'''-penta-N-tert-butoxycarbonyl-4",6"-di-iodo-1-N-(L-4-amino-2-hydroxybutyryl)-dibekacin (which gave a single spot at Rf 0.40 in a silica gel thin layer chromatography developed with chloroform-ethanol (30:1)) and a minor proportion of the corresponding 6"-mono-iodo product namely, 2",2'''-di-O-benzoyl-3,2',6',3",4'''-penta-N-tert-butoxycarbonyl-6"-mono-iodo-1-N-(L-4-amino-2-hydroxybutyryl)-dibekacin (which gave a single spot at Rf 0.31 in the same silica gel thin layer chromatography just mentioned above).

This powder (220 mg, 0.15 m mol) was dissolved in 5 ml of dioxane, and the solution was subjected to a catalytic hydrogenolysis under a hydrogen pressure of 3.6 Kg/cm$^2$ for 5 hours in a Paar apparatus in the presence of a Raney nickel catalyst (R-200, a product of Nikko Rika Co., Japan) to effect the de-iodination. The reaction solution was filtered to remove the catalyst. The filtrate was concentrated to dryness (169 mg) under reduced pressure, and the residue was taken up into 10 ml of 12% ammonia-methanol. The resulting solution was allowed to stand at ambient temperature overnight to effect the de-benzoylation. The reaction solution was concentrated to dryness (131 mg) under reduced pressure, and the residue was dissolved in 2 ml of aqueous 90% trifluoroacetic acid, followed by being allowed to stand at ambient temperature for 45 minutes to effect the removal of the tert-butoxycarbonyl groups. The reaction solution was concentrated to dryness under reduced pressure and the residue was washed with ethyl ether, affording a faintly yellow powder (comprising the trifluoroacetates of 1-N-(L-4-amino-2-hydroxybutyryl)-4",6"-dideoxy- and 6"-deoxydibekacins). This powder was dissolved in 2 ml of water and adjusted to pH 7.8 by addition of 1 N aqueous ammonia, and the resulting solution was passed through a column of 20 ml of Amberlite CG-50 (NH$_4^+$) for adsorption of the desired products. The Amberlite column was washed with water (68 ml), with 0.2 N aqueous ammonia (70 ml) and then with 0.5 N aqueous ammonia (88 ml), followed by elution with 0.6 N aqueous ammonia (80 ml) and then with 0.7 N aqueous ammonia (50 ml). The eluate from the elution with the 0.6 N aqueous ammonia were combined together and concentrated to dryness under reduced pressure to give 7.2 mg (yield 8%) of a colorless powder of 1-N-(L-4-amino-2-hydroxybutyryl)-6''-deoxydibekacin (as the sesqui-carbonate). The fractions from the elution with the 0.7 N aqueous ammonia were combined together and concentrated to dryness under reduced pressure to give 18.8 mg (yield 21%) of a colorless powder of 1-N-(L-4-amino-2-hydroxybutyryl)-4'',6''-dideoxydibekacin (as the sesqui-carbonate). This product decomposed at 142°~147° C. and gave a specific optical rotation $[\alpha]_D^{24} = +84°$ (c 0.5, water).

EXAMPLE 4

Synthesis of 1-N-(L-4-amino-2-hydroxybutyryl)-6''-deoxydibekacin

6''-Deoxydibekacin (as the sesqui-carbonate) (26.4 mg, 0.05 m mol) obtained in the Example 2 was dissolved in 0.5 ml of anhydrous dimethylsulfoxide, and the resulting solution was admixed with 54.7 mg (0.24 m mol) of zinc acetate ($Zn(CH_3CO_2)_2 \cdot 2H_2O$) and stirred at ambient temperature for 20 hours to effect the formation of the complex of 6''-deoxydibekacin with zinc cation. The solution containing said complex was admixed with 41.2 mg (0.165 m mol) of benzyloxycarbonyl-N-hydroxysuccinimide ester, and the admixture was agitated for 20 hours at ambient temperature to effect the benzyloxycarbonylation of the 3-, 2'- and 6'-amino groups of 6''-deoxydibekacin which were not complexing with the zinc cation. The reaction solution was admixed with 30 ml of water and a small volume of concentrated aqueous ammonia so that the reaction solution was adjusted to pH 11, whereby the breakdown of the zinc-complexing with the 3,2',6'-tri-N-benzyloxycarbonylated 6''-deoxydibekacin was effected. The reaction solution so treated which contained the precipitate as formed was filtered, and the precipitate collected (which comprised the 3,2',6'-tri-N-benzyloxycarbonyl-6''-deoxydibekacin) was dissolved in 5 ml of dimethylsulfoxide. To the resultant solution was added a solution of 0.02 ml (0.14 m mol) of ethyl trifluoroacetate in 1 ml of dimethylsulfoxide, followed by agitation at ambient temperature for 3 hours to effect the selective 3''-N-trifluoroacetylation and to give the reaction solution containing 3,2',6'-tri-N-benzyloxycarbonyl-3''-N-trifluoroacetyl-6''-deoxydibekacin. This reaction solution was admixed with 0.01 ml (0.07 m mol) of triethylamine and with 26.3 mg (0.075 m mol) of N-hydroxysuccinimide ester of L-4-benzyloxycarbonylamino-2-hydroxybutyric acid, and the admixture obtained was stirred for 15 hours at ambient temperature to effect the acylation of the 1-amino group of the 6''-deoxydibekacin compound. The reaction mixture was admixed with 2 ml of aqueous saturated sodium chloride and 2 ml of ethyl acetate, and the ethyl acetate phase together with the precipitate formed was concentrated to dryness to give 44.2 mg of a powder. This powder was admixed with 2 ml of a mixture of tetrahydrofuran and 1 N aqueous ammonia (1:1 by volume), and the resultant admixture was stirred at ambient temperature for 20 hours to effect the removal of the trifluoroacetyl group. The reaction solution obtained was concentrated to a small volume, followed by addition of 2 ml of 1 N aqueous ammonia thereto. The precipitate formed was removed by filtration and washed with water. This precipitate was dissolved in 20 ml of a mixture of acetic acid, methanol and water (2:1:1 by volume), and the resulting solution, after addition of 50 mg of 5% palladium-on-carbon thereto, was subjected to catalytic hydrogenolysis by passage of a hydrogen stream through said solution for 6 hours at ambient temperature. The reaction mixture was filtered to remove the catalyst therefrom, and the filtrate was concentrated to dryness under reduced pressure. The residue was taken up into 0.3 ml of water and the aqueous solution was adjusted to pH 7.8 by addition of 1 N aqueous ammonia. This solution was charged into a column of 2 ml of Amberlite CG-50 ($NH_4^+$ form) for adsorption of the desired product. The column was then washed with 5 ml of water and with 5 ml of 0.1 N aqueous ammonia, followed by elution with 5 ml of 0.5 N aqueous ammonia and then with 10 ml of 0.8 N aqueous ammonia. The fractions from the elution with the 0.8 N aqueous ammonia were combined together and concentrated to dryness under reduced pressure to give 10.0 mg of a colorless powder of the desired 1-N-(L-4-amino-2-hydroxybutyryl)-6''-deoxydibekacin (sesqui-carbonate). Yield 32%. This product decomposed at 132°~139° C. and gave a specific optical rotation $[\alpha]_D^{23} = +73°$ (c 0.3, water).

EXAMPLE 5

Synthesis of 1-N-(L-4-amino-2-hydroxybutyryl)-4'',6''-dideoxydibekacin

The process of the above Example 4 was repeated using 25.6 mg (0.05 m mol) of 4'',6''-dideoxydibekacin sesqui-carbonate instead of the 6''-deoxydibekacin. A colorless powder of 1-N-(L-b 4-amino-2-hydroxybutyryl)-4'',6''-dideoxydibekacin (sesqui-carbonate) was obtained. Yield 9.0 mg (29%).

What we claim is:

1. A compound of the formula (I)

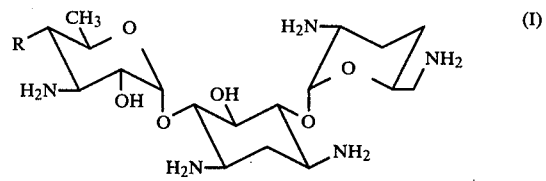

wherein R is a hydroxyl group or a hydrogen atom, or an acid addition salt thereof.

2. The compound of claim 1 which is 6''-deoxydibekacin, or a pharmaceutically acceptable acid addition salt thereof.

3. The compound of claim 1 which is 4'',6''-dideoxydibekacin, or a pharmaceutically acceptable acid addition salt thereof.

4. A compound of the formula (II)

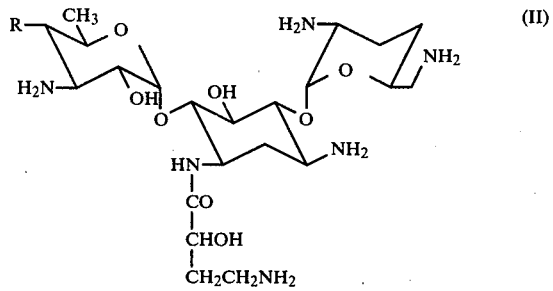

wherein R is a hydroxyl group or a hydrogen atom, or a pharmaceutically acceptable acid addition salt thereof.

5. The compound of claim 4 which is 1-N-(L-4-amino-2-hydroxybutyryl)-6"-deoxydibekacin, or a pharmaceutically acceptable acid addition salt thereof.

6. The compound of claim 4 which is 1-N-(L-4-amino-2-hydroxybutyryl)-4",6"-dideoxydibekacin, or a pharmaceutically acceptable acid addition salt thereof.

7. An antibacterial composition comprising as the active ingredient 6"-deoxydibekacin, 4",6"-dideoxydibekacin, 1-N-(L-4-amino-2-hydroxybutyryl)-6"-deoxydibekacin or 1-N-(L-4-amino-2-hydroxybutyryl)-4",6"-dideoxydibekacin or a pharmaceutically acceptable acid addition salt thereof, in an antibacterially effective amount to inhibit the growth of bacteria, in combination with a carrier for the active ingredient compound.

8. A compound which is selected from the group consisting of 2'''-O-benzoyl-1,3,2',6',3''-penta-N-tert-butoxycarbonyl-4'',6''-di-iodo-dibekacin and 2''-O-benzoyl-1,3,2',6',3''-penta-N-tert-butoxycarbonyl-6''-iodo-dibekacin.

9. A compound which is selected from the group consisting of 2'',2'''-di-O-benzoyl-3,2',6',3'',4'''-penta-N-tert-butoxycarbonyl-4'',6''-di-iodo-1-N-(L-4-amino-2-hydroxybutyryl)-dibekacin and 2'',2'''-di-O-benzoyl-3,2',6',3'',4'''-penta-N-tert-butoxycarbonyl-6''-mono-iodo-1-N-(1-4-amino-2-hydroxybutyryl)-dibekacin.

* * * * *